United States Patent
Jung et al.

(10) Patent No.: US 11,369,304 B2
(45) Date of Patent: Jun. 28, 2022

(54) SYSTEM AND METHOD FOR VOLITIONAL ELECTROMYOGRAPHY SIGNAL DETECTION

(71) Applicant: ELECTRONICS AND TELECOMMUNICATIONS RESEARCH INSTITUTE, Daejeon (KR)

(72) Inventors: Joon Young Jung, Daejeon (KR); Bae Sun Kim, Daejeon (KR); Yong Ki Son, Daejeon (KR); Dong Woo Lee, Daejeon (KR); Ja Beom Gu, Sejong (KR); Hyung Cheol Shin, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 418 days.

(21) Appl. No.: 16/208,230

(22) Filed: Dec. 3, 2018

(65) Prior Publication Data
US 2019/0200891 A1   Jul. 4, 2019

(30) Foreign Application Priority Data

Jan. 4, 2018 (KR) .................. 10-2018-0001218
Nov. 20, 2018 (KR) .................. 10-2018-0143610

(51) Int. Cl.
*A61B 5/296* (2021.01)
*A61N 1/36* (2006.01)
(Continued)

(52) U.S. Cl.
CPC .............. *A61B 5/296* (2021.01); *A61B 5/316* (2021.01); *A61B 5/7217* (2013.01);
(Continued)

(58) Field of Classification Search
CPC ....... A61B 5/296; A61B 5/316; A61B 5/7217; A61B 5/0022; A61B 5/7475; A61B 5/725;
(Continued)

(56) References Cited

U.S. PATENT DOCUMENTS

2005/0283055 A1   12/2005  Shirai et al.
2011/0009729 A1   1/2011   Shin et al.
(Continued)

FOREIGN PATENT DOCUMENTS

CN   1711961 A   12/2005
CN   1720858 A   1/2006
(Continued)

OTHER PUBLICATIONS

Sennels S, Biering-Srensen F, Andersen OT, Hansen SD. Functional neuromuscular stimulation controlled by surface electromyographic signals produced by volitional activation of the same muscle: adaptive removal of the muscle response from the recorded EMG-signal. IEEE Trans Rehabil Eng. 1997 (Year: 1997).*

(Continued)

*Primary Examiner* — Sean P Dougherty
*Assistant Examiner* — Kyle W. Kretzer

(57) ABSTRACT

Disclosed herein are a system and a method for volitional electromyography (vEMG) signal detection from an EMG signal when functional electrical stimulation (FES) is applied. The system for vEMG signal detection includes a receiver for receiving data from an EMG electrode when FES is applied, a memory for storing a program for detecting a vEMG signal using the received data, and a processor for executing the program, wherein the processor cuts the data received from the EMG electrode disposed at a predetermined position, calculates a difference between data for (Continued)

previous FES and data for current FES, and detects the vEMG signal using the calculated difference.

11 Claims, 8 Drawing Sheets

(51) Int. Cl.
    *A61B 5/00*       (2006.01)
    *A61N 1/04*       (2006.01)
    *A61B 5/316*     (2021.01)

(52) U.S. Cl.
    CPC .......... *A61N 1/0452* (2013.01); *A61N 1/0476* (2013.01); *A61N 1/36003* (2013.01); *A61N 1/36014* (2013.01); *A61B 5/0022* (2013.01); *A61B 5/725* (2013.01); *A61B 5/7475* (2013.01)

(58) Field of Classification Search
    CPC .... A61B 5/389; A61N 1/0452; A61N 1/0476; A61N 1/36003; A61N 1/36014
    See application file for complete search history.

(56) References Cited

U.S. PATENT DOCUMENTS

| | | | |
|---|---|---|---|
| 2015/0272483 A1 | 10/2015 | Etemad et al. | |
| 2016/0144172 A1* | 5/2016 | Hsueh | A61N 1/36003 607/48 |
| 2017/0238865 A1 | 8/2017 | Youm et al. | |

FOREIGN PATENT DOCUMENTS

| | | |
|---|---|---|
| CN | 104394762 A | 3/2015 |
| CN | 105054927 A | 11/2015 |
| CN | 106693178 A | 5/2017 |
| JP | 2004000698 A | 1/2004 |
| KR | 1020160119515 A | 10/2016 |
| KR | 1020160127872 A | 11/2016 |

OTHER PUBLICATIONS

Hojun Yeom et al., "Autogenic EMG-controlled functional electrical stimulation for ankle dorsiflexion control", Journal of Neuroscience Methods, 2010, pp. 118-125, Elsevier B.V.

Joonyoung Jung et al., "Dual Channel Volitional Electromyography(vEMG) Signal Estimation Algorithm During Functional Electrical Stimulation(FES)", Annual Conference of the International Functional Electrical Stimulation Society, Aug. 28-3, 2018, Nottwil Switzerland, pp. 21-24.

Yukihiro Hara et al., "Hybrid Power-Assisted Functional Electrical Stimulation to Improve Hemiparetic Upper-Extremity Function", American Journal of Physical Medicine & Rehabilitation, Dec. 2006, pp. 977-985.

H. Matsuse, et al. "Muscle training by means of combined electrical stimulation and volitional contractions", Aviation Space an Environmental Medicine, Jun. 2006; 77(6):581-5.

Chinese Office Action for related application CN 20191001599.3, dated May 7, 2021.

* cited by examiner

SYSTEM AND METHOD FOR VOLITIONAL ELECTROMYOGRAPHY SIGNAL DETECTION

CROSS-REFERENCE TO RELATED APPLICATION

This application claims priority to and the benefit of Korean Patent Application No. 10-2018-0001218, filed on Jan. 4, 2018, and Korean Patent Application No. 10-2018-0143610, filed on Nov. 20, 2018, the disclosure of which is incorporated herein by reference in its entirety.

BACKGROUND

1. Field of the Invention

The present invention relates to a system and a method for volitional electromyography (vEMG) signal detection from an EMG signal when functional electrical stimulation (FES) is applied.

2. Discussion of Related Art

Detection of a volitional electromyography (vEMG) signal according to the related art requires a blanking circuit as an additional device, a technique for processing an EMG signal has a limitation when a functional electrical stimulation (FES) is applied, and there is a problem in that the detection becomes unstable in a state in which dynamic FES is applied.

SUMMARY OF THE INVENTION

The present invention is directed to a system and a method for volitional electromyography (vEMG) signal detection, which are capable of improving performance of vEMG signal detection irrespective of additional devices, such as a blanking circuit and the like, and capable of robustly detecting the vEMG signal even in a case in which a dynamic functional electrical stimulation (FES) is applied.

According to an aspect of the present invention, there is provided a system for vEMG signal detection, the system including a receiver configured to receive data from an EMG electrode when FES is applied, a memory configured to store a program for detecting a vEMG signal using the received data, and a processor configured to execute the program, wherein the processor may cut the data received from the EMG electrode disposed at a predetermined position, calculate a difference between data for previous FES and data for current FES, and detect the vEMG signal using the calculated difference.

According to another aspect of the present invention, there is provided a method for vEMG signal detection, the method comprising the steps of: (a) receiving data from an EMG electrode attached at a predetermined location, (b) cutting the received data into a predetermined unit and storing the cut data in a buffer, (c) calculating a difference between the data obtained for a previous stimulation and the data obtained for a current stimulation with respect to the data cut into the predetermined unit, and (d) detecting a vEMG signal using the calculated difference obtained in the step (c).

According to still another aspect of the present invention, there is provided a system for vEMG signal detection, the system including a FES electrode configured to apply FES, an EMG electrode attached to a skin surface of a specific muscle to which the FES is applied, and a detector configured to cut data received from a position at which the EMG electrode is attached, calculate a difference between data for previous FES and data for current FES, and detect a vEMG signal.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
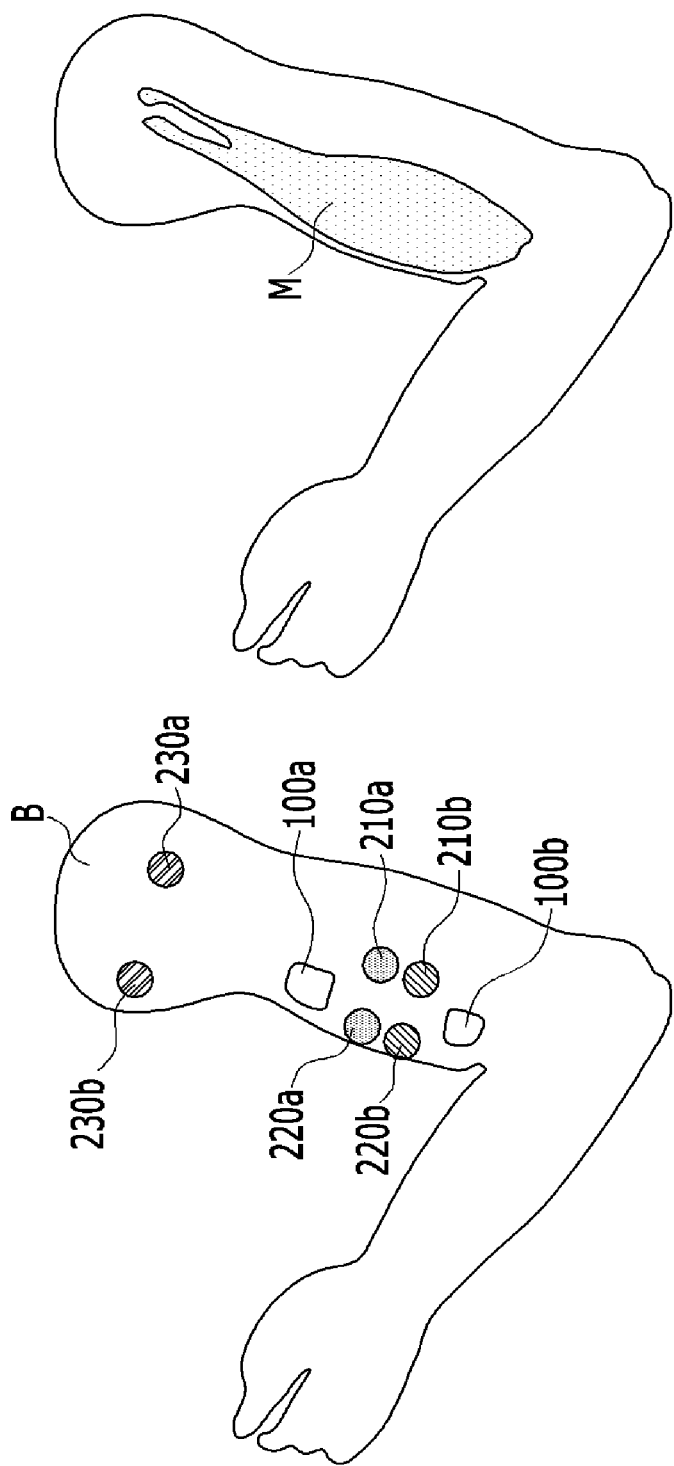
FIG. 1 is a diagram illustrating a system for volitional electromyography (vEMG) signal detection according to an embodiment of the present invention.

The above-described objectives and other objectives, advantages, and features of the present invention and the manner for achieving the same will become apparent with reference to embodiments described in detail below with the accompanying drawings.

However, the present invention is not limited to the embodiments disclosed below and may be implemented in many different forms, the following embodiments are merely provided to allow those skilled in the art to which the present invention pertains to easily understand the objectives, configurations, and effects of the present invention, and the scope of the present invention is defined by the appended claims.

Meanwhile, terms used herein are intended to describe the embodiments and are not intended to limit the present invention. In this disclosure, the singular forms include the plural forms unless the context clearly dictates otherwise. It is noted that the terms "comprises" and/or "comprising" used herein do not exclude the presence or addition of one or more other components, steps, operations, and/or elements in addition to stated components, steps, operations, and/or elements.

Hereinafter, in order to aid in understanding of those skilled in the art, the background of the present invention will be described first and then the embodiments of the present invention will be described.

Electromyography (EMG), which measures muscle activity by measuring potential differences generated in muscle cells when the muscle is activated, is a technique which is widely used not only in the medical care field but also in the biomechanics field.

The EMG has been developed according to a configuration of an electrode for measuring a potential difference between activated muscles and a commonly used form of the EMG is an electrode type EMG device which is attached to the skin surface.

Since the underlying technology of an electrical stimulation technique was invented in 1967, the electrical stimulation technique for artificially inducing contraction of muscles by applying electrical stimulation to the muscles in the form of a constant current or a constant voltage have been developed as a method of applying electrical stimulation and in a field relating to the shape and position of an electrode for transferring applied stimulation to muscles, and a commonly used shape is a skin surface electrode shape which is adhered to the skin surface.

The electrical stimulation technique has been developed as a functional electrical stimulation (FES) technique for mainly supplementing and replacing the functions of weakened or lost muscles, and, specifically in recent years, in addition to the purpose of rehabilitation and treatment, electrical muscle stimulation (EMS) fitness training devices have been emerging in order to obtain an exercise effect by utilizing electrical stimulation even when a user does not intentionally exercise.

Generally, an FES device may control stimulation intensity through various variables of applied electrical stimulation, i.e., an amplitude, a frequency, a sustaining time, and a waveform of a stimulation pulse, and this determines a muscle contraction force induced by FES.

There are methods in which such stimulation variables are constantly applied as values predetermined by a user using a FES device and in which such stimulation variables are varied in real time by intervention of the user using the FES device, thereby inducing muscle contraction.

Here, the intervention of the user utilizes a manual switch for which the user applies input as necessary, a position sensor for measuring movement of the user, and, recently, an EMG sensor for measuring muscle activity of the user.

Among the above devices, an EMG-FES device in which the FES device and the EMG are combined and utilized requires the highest technical skills.

The EMG-FES device is classified into an EMG-triggered FES device which observes a time when an EMG signal exceeds a threshold value before FES is applied to apply electrical stimulation of a predetermined variable, and an EMG-controlled FES device which controls a degree of stimulation of the FES device by reflecting an EMG signal that is measured in real time.

1) The EMG-triggered FES device may be implemented to measure a root mean square (RMS) value of an EMG signal of the user before applying FES and compare the RMS value with a predetermined threshold value in real time such that the EMG-triggered FES device has been successfully commercialized with relative ease to be utilized in rehabilitation treatment of stroke patients and in improvement of walking ability of foot drop patients.

Meanwhile, 2) in the case of the EMG-controlled FES device, since a volitional EMG (vEMG) signal of a user is distorted by a stimulation artifact, which is a FES signal, and an M-wave, which is an EMG signal induced by FES, in the EMG signal when the FES is applied, a method of introducing a blanking circuit for blocking an input of the EMG sensor during electrical stimulation and application of a signal processing algorithm is considered by researchers.

An artifact induced by stimulation refers to an amount of a current applied to muscles by the FES signal, and the artifact is significantly larger than an active potential difference between the muscles such as to exceed a typical acceptance range of the EMG signal, thereby distorting meaningful information of the EMG signal.

Further, the M-wave distorts meaningful information of the vEMG signal for several milliseconds while the M-wave is sustained.

The blanking circuit is a device which serves to remove the stimulation artifact by temporarily blocking an EMG amplifier, which amplifies a minute active potential difference between muscles to an effective measurement range, according to a frequency of a FES signal being applied.

An EMG signal, in which the stimulation artifact is removed from the EMG signal through the blanking circuit when FES is applied, may be interpreted as the sum of an M-wave and a vEMG signal.

Generally, a vEMG detection algorithm for implementing the EMG-controlled FES device necessarily utilizes the blanking circuit.

A signal processing algorithm of the related art, which detects a vEMG signal from an EMG signal when FES is applied, is an algorithm applied to a signal from which the stimulation artifact is removed through the above-mentioned blanking circuit, and in order to effectively remove an M-wave, algorithms including a comb filter method, a window blanking method, and a Gram-Schmidt filter method are considered.

The comb filter method is a method of detecting a vEMG signal by removing an EMG signal corresponding to a bandwidth of an M-wave through a filter which is a combination of notch filters having a plurality of cut-off bandwidths. The window blanking method is a method of removing influence due to an M-wave by not receiving data during an M-wave sustain period in which FES is applied and then sustained for several milliseconds. The Gram-Schmidt filter method is a method of removing an M-wave, which is varied in real time, through an algorithm capable of adjusting the M-wave by applying filter variables.

When the above-described blanking circuit is utilized, an artifact due to stimulation may not be received, but this requires an essential correction to the EMG amplifier such that there are problems in that the blanking circuit is difficult to efficiently apply to a commercial EMG device and unnecessary additional devices are required.

Further, the above-described signal processing algorithm is relatively useful for detecting a vEMG signal in a limited situation, but the comb filter method is insufficient to be adapted to a situation in which the FES signal is dynamically varied because the M-wave is assumed as a fixed variable.

The window blanking method has problems in that a frequency of the FES should be fixed and the vEMG signal is also removed in the process of removing the M-wave such that a detection resolution is significantly degraded.

Like the comb filter method, the Gram-Schmidt filter method is insufficient to be perfectly adapted to the situation in which the FES signal is dynamically varied.

Specifically, the M-wave is determined by the FES signal, but the M-wave and the FES signal have a non-linear relationship, and in a situation in which the FES signal is dynamically varied, non-linearity between the M-wave and the FES signal is maximized and thus there is a problem in that a vEMG signal is difficult to predict such that there is a problem of limiting muscle control performance of the EMG-controlled FES device which controls FES on the basis of the predicted vEMG signal.

The present invention has been proposed in order to solve the above-mentioned problems, and an objective of the present invention is to provide a device and a method which are capable of detecting a volitional muscle contraction intent from an EMG signal and are capable of distinguishing a degree of contraction caused by electrical stimulation from a degree of contraction caused by a volitional intent from an EMG signal which is distorted and measured when FES is applied.

Further, the objective of the present invention is to provide a system and a method which are capable of improving performance of vEMG signal detection irrespective of additional devices such as a blanking circuit and the like and capable of robustly detecting the vEMG signal even in a situation in which a dynamic FES is applied.

The present invention is derived from the research carried out as part of the information communication and broadcasting R&D project (Project No. 1711055381, entitled "Source Technology Development for Enhancing Auditory and Muscle Strength of Human for Abnormality or Degradation of Body Function) of the Ministry of Science and Information and Communications Technology (ICT) and the Institute for Information and Communications Technology Promotion.

FIG. 1 is a diagram illustrating a system for vEMG signal detection according to an embodiment of the present invention.

Referring to FIG. 1, the system for vEMG signal detection according to the embodiment of the present invention includes FES electrodes 100a and 100b for applying FES, EMG electrodes 210a, 210b, 220a, and 220b attached to skin surfaces of specific muscles to which the FES is applied, and a detector for cutting data received from attachment positions of the EMG electrodes 210a, 210b, 220a, and 220b and detecting a vEMG signal by calculating a difference between data for previous FES and data for current FES.

According to the embodiment of the present invention, the FES electrodes 100a and 100b and the EMG electrodes 210a, 210b, 220a, and 220b are attached to skin surfaces at positions M of muscles constituting a musculoskeletal system of a region of a user body B.

The pair of FES electrodes 100a and 100b, which are attached to skin surfaces at positions M of specific muscles, are attached in a direction parallel to a direction of a muscle fiber.

An EMG electrode for measuring an EMG signal of the same muscle is configured with two pairs of first EMG electrodes 210a and 210b and second EMG electrodes 220a and 220b, and like the FES electrodes 100a and 100b, the first EMG electrodes 210a and 210b and the second EMG electrodes 220a and 220b are attached in directions parallel to the direction of the muscle fiber.

A first EMG reference electrode 230a and a second EMG reference electrode 230b, which respectively serve as reference electrodes of the first EMG electrodes 210a and 210b and the second EMG electrodes 220a and 220b, are attached at positions irrelevant to corresponding muscles.

The detector according to the embodiment of the present invention cuts data received from the first EMG electrodes 210a and 210b and the second EMG electrodes 220a and 220b in consideration of a length of a frequency of the FES. In this case, the data is configured as the sum of a stimulation artifact, an M-wave, and a vEMG signal.

The detector calculates the difference between the data for the previous FES and the data for the current FES to remove influence (the stimulation artifact and the M-wave) due to synchronous contraction according to application of FES.

The FES electrodes 100a and 100b according to the embodiment of the present invention are a pair of electrodes for applying dynamic FES, the EMG electrodes 210a, 210b, 220a, and 220b are two pairs of EMG electrodes for measuring EMG signals when the dynamic FES is applied, and the detector receives data for the previous FES and data for the current FES from each of the first EMG electrodes 210a and 210b and the second EMG electrodes 220a and 220b, calculates the difference between the data for the previous FES and the data for the current FES, and removes influence due to dynamic FES, thereby detecting a vEMG signal.

Hereinafter, the vEMG signal according to the embodiment of the present invention will be described in more detail with reference to FIGS. 2 and 3.

Figure 2:
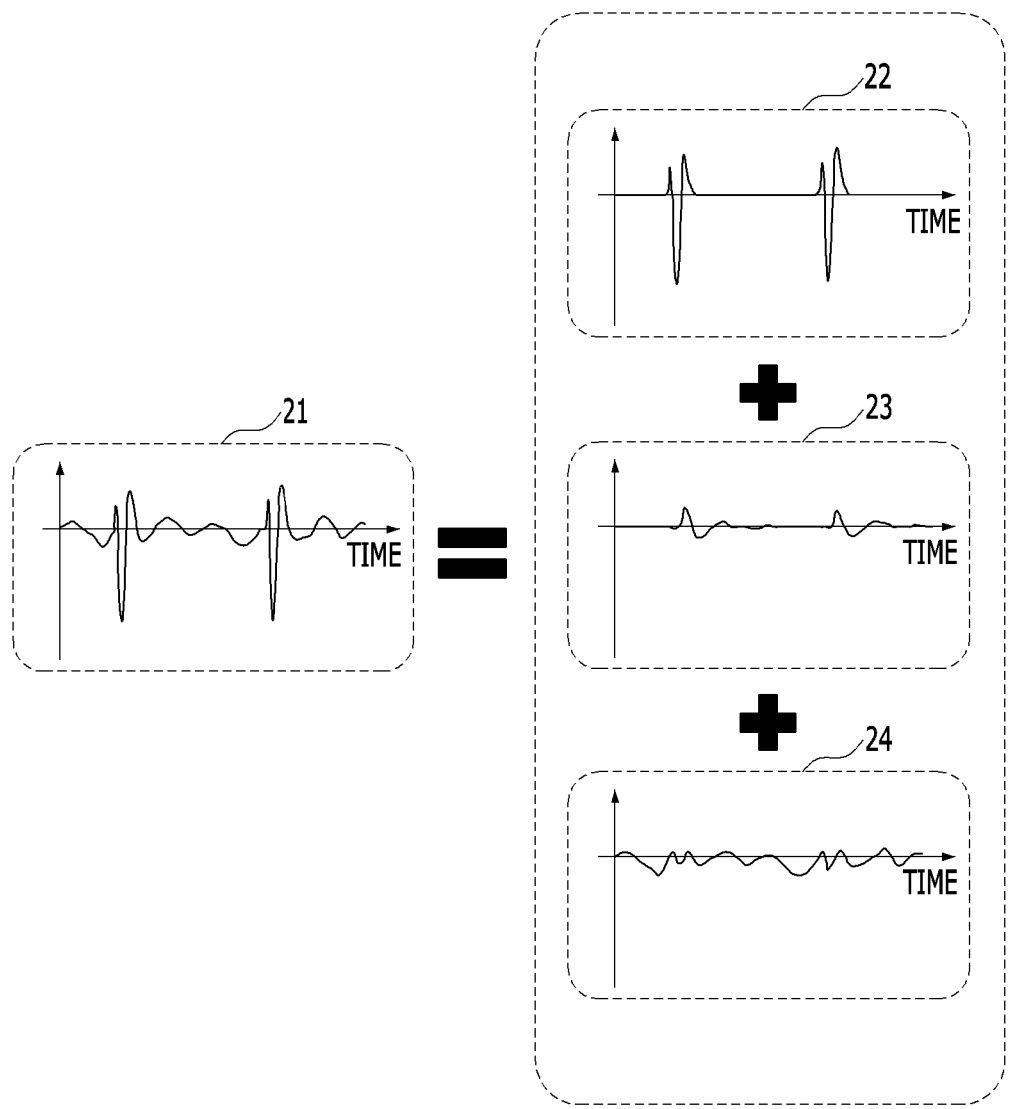
FIG. 2 is a diagram illustrating EMG raw data according to an embodiment of the present invention.

FIG. 2 is a diagram illustrating EMG raw data according to the embodiment of the present invention and shows a configuration of an EMG signal when FES is applied.

Referring to FIG. 2, EMG raw data 21 when FES is applied has a value of the linear sum of a stimulation artifact 22, an M-wave 23, and a vEMG signal 24.

According to the embodiment of the present invention, a relationship of the linear sum shown in FIG. 2 ignores influence of noise due to external factors, and the influence thereof may be ignored according to the embodiment of the present invention, which will be described below.

In both cases in which muscles are activated by a volitional intent and by artificial FES, minute activation potentials, which can be measured by an EMG device, are generated and have different characteristics according to a physiological property of a human body.

When the muscles are activated by a volitional intent, muscle fibers asynchronously contract with difference synchronization in arbitrary order to maximize efficiency of the muscles.

On the other hand, when artificial muscle contraction is caused by FES, the muscle fibers contract simultaneously and synchronously by applying electrical stimulation through a skin surface.

Referring to FIG. 2, the stimulation artifact 22 and the M-wave 23 are the results of synchronous contraction, and the vEMG signal 24 is the result of asynchronous contraction.

According to such characteristics of the signals, the stimulation artifact 22 and the M-wave of the EMG signal when the FES is applied show the same tendency irrespective of positions of the muscles activated by the FES.

On the other hand, the vEMG signal 24, which is the result of the asynchronous contraction by the volitional intent, tends to vary according to the positions of the muscles.

Specifically, due to such a characteristic, the vEMG signal 24 is sufficient to be assumed as a Gaussian random signal.

Figure 3:
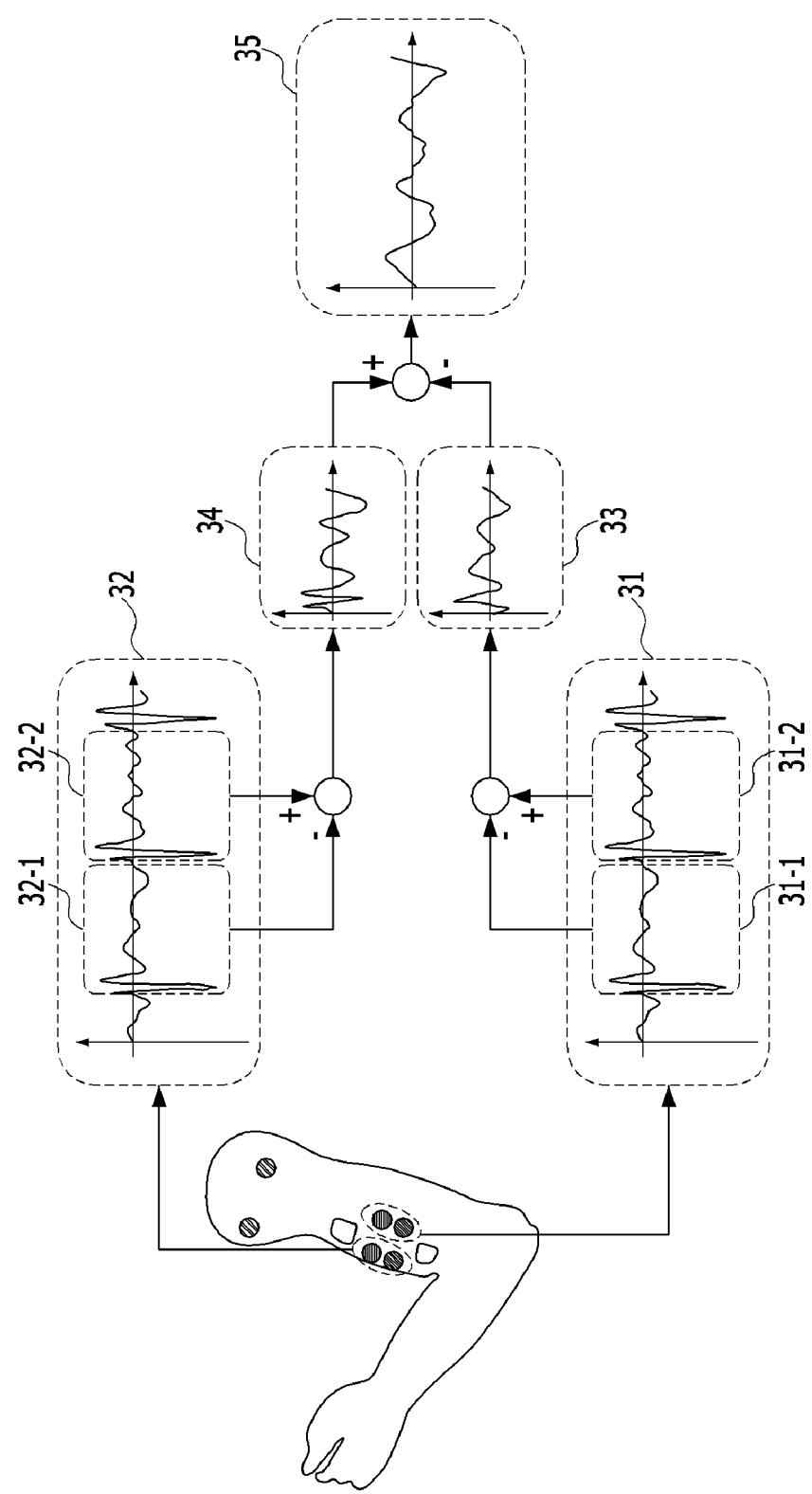
FIG. 3 is a diagram illustrating a process of detecting a vEMG signal according to an embodiment of the present invention.

FIG. 3 is a diagram illustrating a process of detecting a vEMG signal according to an embodiment of the present invention.

In order to detect a vEMG signal in a situation in which FES is applied, as shown in FIG. 1, two pairs of EMG electrodes, such as the first EMG electrodes 210a and 210b and the second EMG electrodes 220a and 220b, are attached within a range of the muscles to which the FES is being applied. This is because of fully utilizing physiological properties of the muscles due to the FES.

FIG. 3 shows EMG raw data 31 obtained from the first EMG electrodes 210a and 210b in real time and EMG raw data 32 obtained from the second EMG electrodes 220a and 220b in real time.

In this case, EMG raw data 31-1 of the first EMG electrode when $(i-1)^{th}$ FES is applied, EMG raw data 31-2 of the first EMG electrode when $i^{th}$ FES is applied, EMG raw data 32-1 of the second EMG electrode when the $(i-1)^{th}$ FES is applied, and EMG raw data 32-2 of the second EMG electrode when the $i^{th}$ FES is applied are stored in a buffer according to a length of a frequency of the FES.

A length of the buffer is determined according to a frequency of the FES without a particular limitation.

As shown in FIG. 3, a difference between EMG raw data for current FES and EMG raw data for previous FES is calculated for each of the first EMG and the second EMG such that an EMG raw data difference 33 between the current FES and the previous FES is obtained for the first EMG electrode, and an EMG raw data difference 34 between the current FES and the previous FES is obtained for the second EMG electrode. Through only such a process, influence due to synchronous contraction, i.e., influence of a stimulation artifact and an M-wave, may be removed.

Meanwhile, since a difference between Gaussian random signal is calculated in the above-described process, a tendency of a vEMG signal is maintained to be constant. Therefore, as described above, when a constant FES is applied, the stimulation artifact and the M-wave are significantly removed such that it is possible to detect a vEMG signal.

However, when the FES is dynamically varied, stimulation artifacts and M-waves for the current FES and the previous FES are varied to distort the vEMG signal. According to the embodiment of the present invention, it is possible to detect a vEMG signal 35 and completely remove influence due to the dynamic FES by calculating a difference between calculated values after the same process is performed in the two pairs of the first and second EMG electrodes.

This is because, since the stimulation artifacts and the M-waves formed by the dynamic FES are the results of synchronous contraction according to the same dynamic FES, the first and second EMG electrodes have the same tendency of variation and, as described above, the vEMG signal is the Gaussian random signal such that a tendency of the vEMG signal is maintained even when the difference is calculated.

Figure 4A:
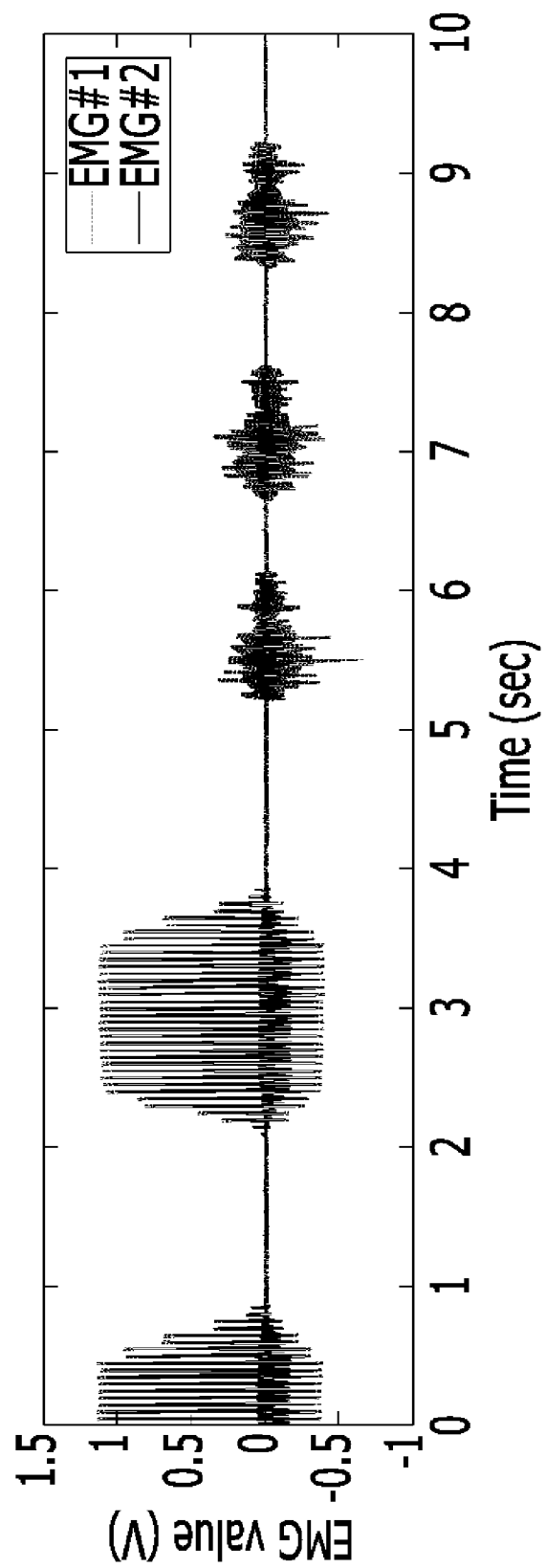
FIG. 4A and FIG. 4B show test results of vEMG signal detection by a comb filter method according to a related art and the system for vEMG signal detection according to the embodiment of the present invention.
Figure 4B:
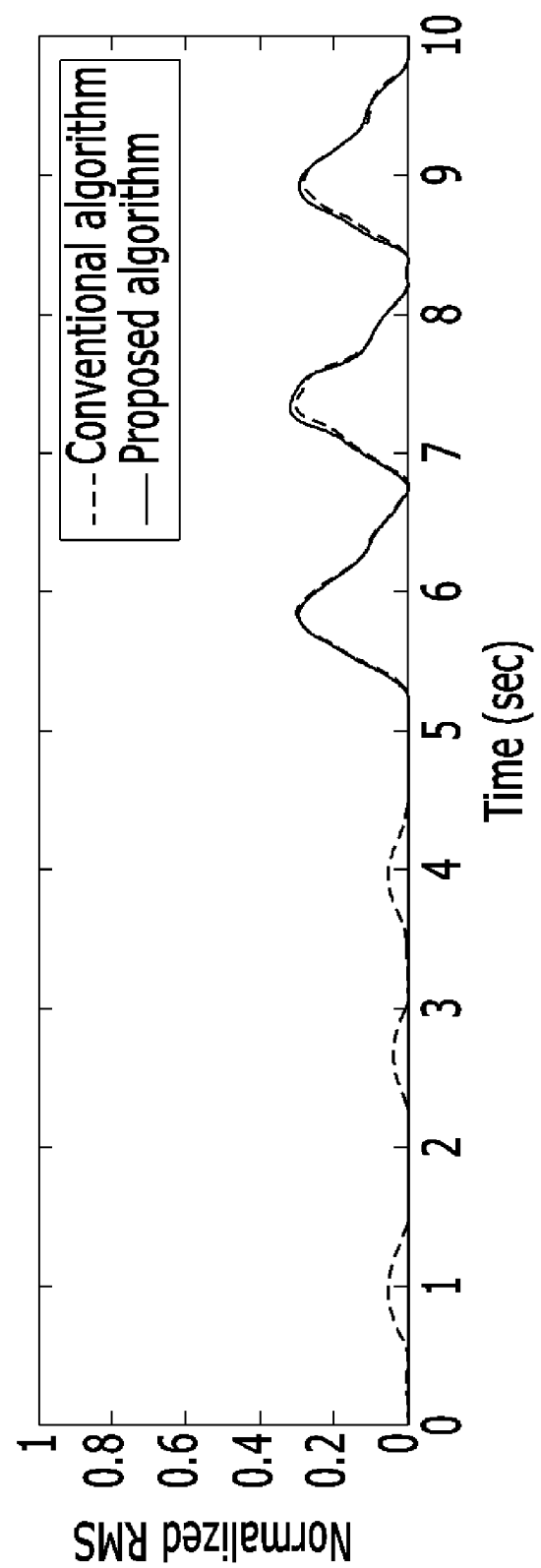

FIG. 4A and FIG. 4B shows test results of vEMG signal detection by a comb filter method according to a related art and the system for vEMG signal detection according to the embodiment of the present invention.

Referring to FIG. 4A and FIG. 4B, a test was carried out by observing whether a vEMG signal was sustained at zero by applying only FES without giving strength to the muscles for the first 5 seconds, and then measuring the vEMG signal by giving strength to the muscles for 5 seconds, and the measured results are shown.

FIG. 4A shows raw data measured from each of the first and second EMG electrodes, and FIG. 4B shows a comparison of test results obtained by applying a conventional comb filter method and the system for vEMG signal detection according to the embodiment of the present invention.

As shown in FIG. 4B, in a section in which FES is dynamically varied such that the stimulation artifact is varied, it can be seen that the vEMG signal is distorted due to the variation in FES according to the conventional comb filter method, whereas a value of the vEMG signal is sustained at zero irrespective of the variation in FES according to the embodiment of the present invention.

Figure 5:
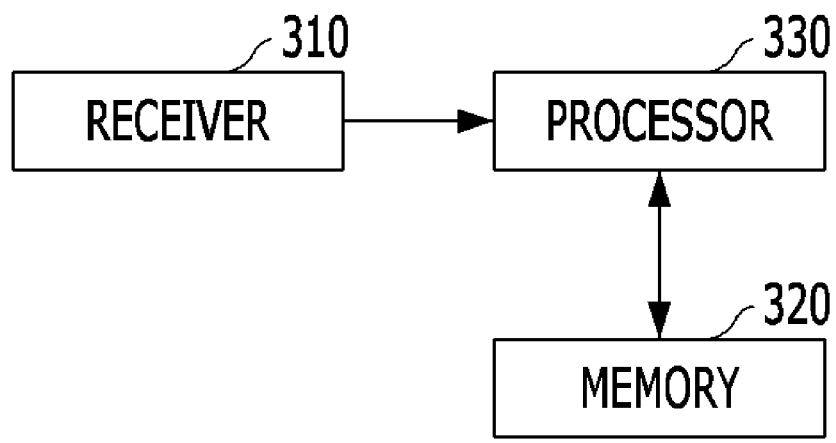
FIG. 5 is a block diagram illustrating the system for vEMG signal detection according to the embodiment of the present invention.

FIG. 5 is a block diagram illustrating the system for vEMG signal detection according to the embodiment of the present invention.

The system for vEMG signal detection according to the embodiment of the present invention includes a receiver 310 for receiving data from an EMG electrode when FES is applied, a memory 320 for storing a program for detecting a vEMG signal using the received data, and a processor 330 for executing the program. The processor 330 cuts the data received from the EMG electrode disposed at a predetermined position, calculates a difference between data for previous FES and data for current FES, and detects the vEMG signal using the calculation result.

As described above with reference to FIG. 1, at least two pairs of EMG electrodes are attached in a direction parallel to a direction of a corresponding muscle fiber to which FES is applied by a FES electrode, and the receiver 310 receives EMG raw data configured with the linear sum of a stimulation artifact, an M-wave, and a vEMG signal.

The processor 330 according to the embodiment of the present invention cuts the EMG raw data according to a length of a frequency of the FES and stores the cut EMG raw data in a buffer, calculates a difference between the EMG raw data for the previously applied FES and the EMG raw data for the currently applied FES, and removes influence due to stimulation artifacts and M-waves.

As described above with reference to FIG. 1, the processor 330 calculates a difference between the data difference value calculated from the first EMG electrodes and the data difference value calculated from the second EMG electrodes, removes influence due to the FES which is dynamically varied, and detects a vEMG signal.

Figure 6:
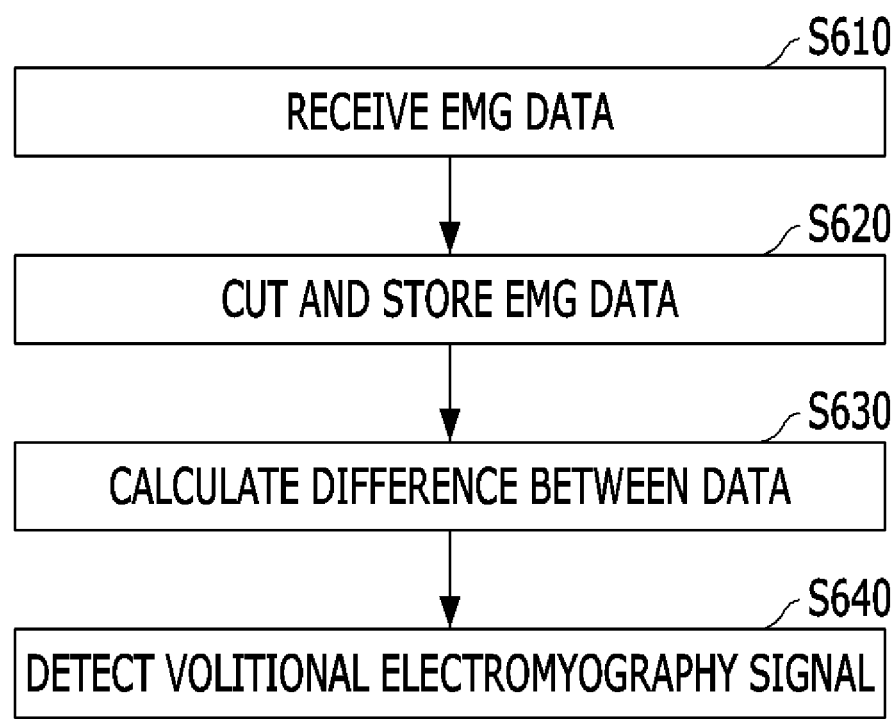
FIG. 6 is a flowchart illustrating a method for vEMG signal detection according to an embodiment of the present invention.

FIG. 6 is a flowchart illustrating a method for vEMG signal detection according to an embodiment of the present invention.

The method for vEMG signal detection according to the embodiment of the present invention includes receiving data from an EMG electrode attached at a predetermined position (S610), cutting the data into predetermined units and storing the cut data in a buffer (S620), calculating a difference between data obtained for previous FES and data obtained for current FES with respect to the data cut into the predetermined units (S630), and detecting a vEMG signal using the obtained calculated difference value (S640).

In operation S610, the data is received from the EMG electrode which is attached to a skin surface of a corresponding muscle to which FES is applied in a direction parallel to a direction of a muscle fiber.

In operation S610, EMG raw data configured with the linear sum of a stimulation artifact, an M-wave, and the vEMG signal is received.

In operation S620, the EMG raw data is cut into predetermined units in consideration of a frequency of FES, and in operation S630, a difference between the EMG raw data for the previously applied FES and the EMG raw data for the currently applied FES is calculated to remove a result due to synchronous contraction.

In operation S630, a difference between the EMG raw data for the previously applied FES and the EMG raw data for the currently applied FES is calculated with respect to the EMG raw data obtained from each of a first EMG electrode and a second EMG electrode. In operation S640, a difference between the calculated differences is calculated and influence due to dynamic FES is removed to detect the vEMG signal.

Meanwhile, the method for vEMG signal detection according to the embodiments of the present invention may be implemented in a computer system or may be recorded in a recording medium. The computer system may include one or more processors, a memory, a user input device, a data communication bus, a user output device, and a storage device. Each of the above-described components performs data communication via the data communication bus.

The computer system may further include a network interface coupled to a network. The processor may be a central processing unit (CPU) or a semiconductor device which processes commands stored in the memory and/or the storage device.

The memory and the storage device may include various forms of volatile or nonvolatile storage media. For example, the memory may include a read only memory (ROM) and a random access memory (RAM).

Therefore, the method for vEMG signal detection according to the embodiments of the present invention may be implemented in a computer-executable method. When the method for vEMG signal detection according to the embodiments of the present invention is performed in a computer device, computer-readable commands may perform the detection method according to the present invention.

Meanwhile, the above-described method for vEMG signal detection according to the present invention may be implemented as a computer-readable code in a computer-readable recording medium. The computer-readable recording medium includes all kinds of recording media storing data which are decipherable by the computer system. For example, there may be a ROM, a RAM, a magnetic tape, a magnetic disk, a flash memory, an optical data storage device, and the like. Further, the computer-readable recording medium may be distributed in a computer system connected to a computer network and may be stored and executed as a code readable in a distributed manner.

According to the embodiments of the present invention, unlike the related art, there is no need for additional devices such as a blanking circuit, and there is an effect of being able to improve detection performance of a vEMG signal and being able to be commercialized by being applied to commercial FES and EMG devices.

According to the embodiments of the present invention, it is possible to robustly detect the vEMG signal even in a situation in which FES variables such as an amplitude, a frequency, a sustaining time, and a waveform of a stimulation pulse are dynamically varied such that there is an effect of being capable of maximizing control performance of muscles through FES by being applied to an EMG-controlled FES device.

The effects of the present invention are not limited to the above-mentioned effects, and other effects not mentioned above can be clearly understood by those skilled in the art from the foregoing description.

The embodiments of the present invention have been described. It may be understood by those skilled in the art to which the present invention pertains that the present invention can be implemented in modified forms without departing from the essential feature of the present invention. Therefore, the disclosed embodiments should be considered as an illustrative rather than a determinative. The scope of the present invention is defined by the appended claims rather than by the foregoing description, and all differences within the scope of equivalents thereof should be construed as being included in the present invention.

The present invention described above may be embodied as computer-readable code on a program recording medium. The computer-readable medium includes all types of storage devices configured to store data that can be read by a computer system. Examples of the computer-readable medium include a hard disk drive (HDD), a solid-state drive (SSD), a silicon disk drive (SDD), a read-only memory (ROM), a random-access memory (RAM), a compact disc (CD)-ROM, a magnetic tape, a floppy disk, an optical data storage device, and the like. In addition, the computer-readable medium may be implemented in the form of a carrier wave (e.g., transmission through the Internet).

Figure 7:
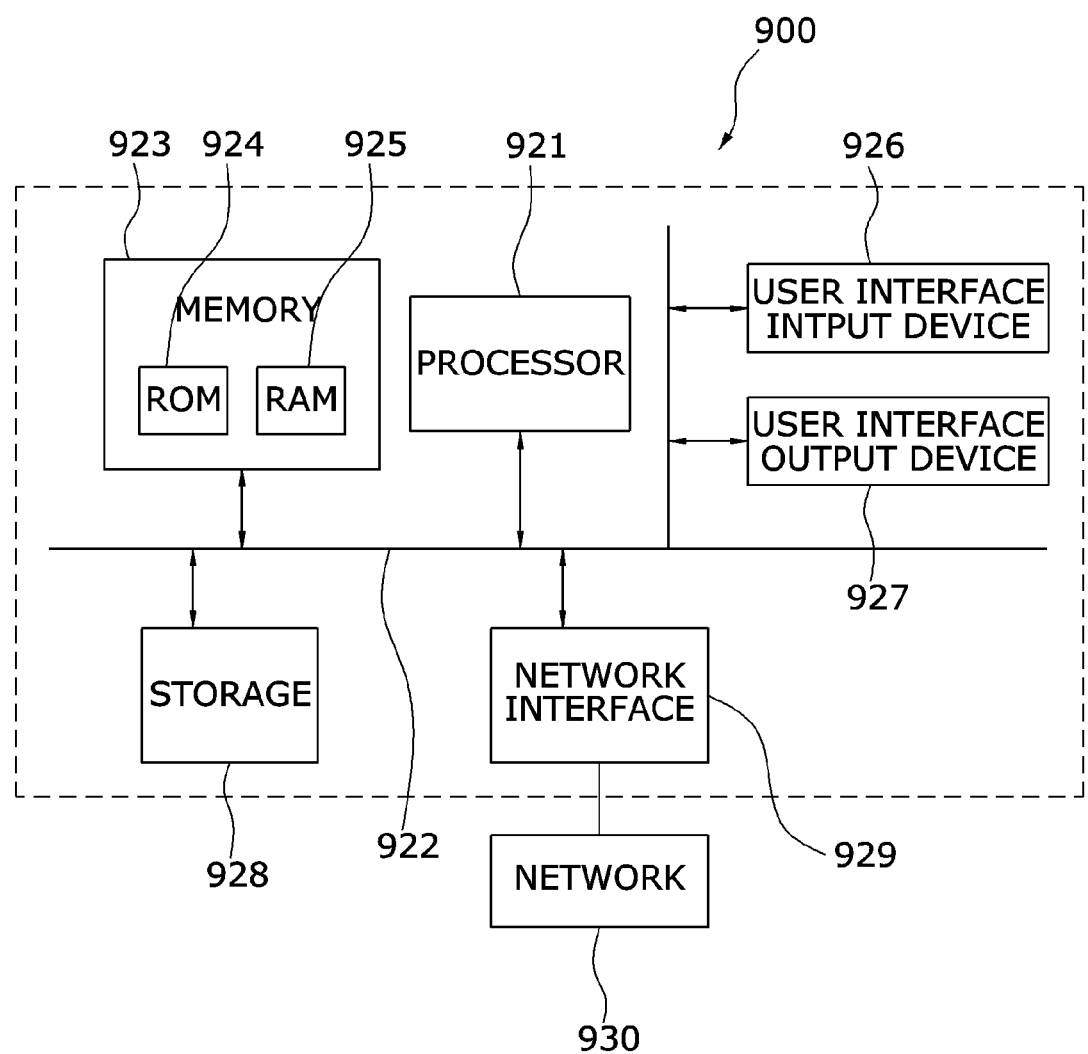
FIG. 7 is a view illustrating an example of a computer system in which a method according to an embodiment of the present invention is performed.

The method according to an embodiment of the present invention may be implemented in a computer system or may be recorded in a recording medium. FIG. 7 illustrates a simple embodiment of a computer system 900. As illustrated, the computer system 900 may include one or more processors 921, a memory 923, a user input device 926, a data communication bus 922, a user output device 927, a storage 928, and the like. These components perform data communication through the data communication bus 922.

Also, the computer system 900 may further include a network interface 929 coupled to a network. The processor 921 may be a central processing unit (CPU) or a semiconductor device that processes a command stored in the memory 923 and/or the storage 928.

The memory 923 and the storage 928 may include various types of volatile or non-volatile storage mediums. For example, the memory 923 may include a ROM 924 and a RAM 925.

Thus, the method according to an embodiment of the present invention may be implemented as a method that can be executable in the computer system 900. When the method according to an embodiment of the present invention is performed in the computer system 900, computer-readable commands may perform the method according to the present invention.

The method according to the present invention may also be embodied as computer-readable codes on a computer-readable recording medium. The computer-readable recording medium is any data storage device that may store data which may be thereafter read by a computer system. Examples of the computer-readable recording medium include read-only memory (ROM), random access memory (RAM), CD-ROMs, magnetic tapes, floppy disks, and optical data storage devices. The computer-readable recording medium may also be distributed over network coupled computer systems so that the computer-readable code may be stored and executed in a distributed fashion.

Further, the above description is to be considered illustrative rather than restrictive in all aspects. The scope of the invention is to be interpreted in a sense defined by the appended claims, and the present invention covers all modifications provided they come within the scope of the appended claims and their equivalents.

What is claimed is:

1. A system for volitional electromyography (vEMG) signal detection, the system comprising:
   a receiver configured to receive first data from a first pair of EMG electrodes and second data from a second pair of EMG electrodes; and
   a processor configured to:
   partition the first data into first raw first data from a first period corresponding to a first Functional Electrical Stimulation (FES) and second raw first data from a second period corresponding to a second FES,
   partition the second data into first raw second data corresponding to the first period and second raw second data corresponding to the second period, calculate a first raw data difference by subtracting the first raw first data from the second raw first data, calculate a second raw data difference by subtracting the first raw second data from the second raw second data, and detect the vEMG signal by subtracting the first raw data difference from the second raw data difference, wherein the detected vEMG signal is used to control a degree of stimulation of the FES.

2. The system of claim 1, wherein:

the first pair of EMG electrodes are attached in a direction parallel to a direction of a corresponding muscle fiber to which the FES is applied by a FES electrode;

the second pair of EMG electrodes are attached in the direction parallel to the direction of the corresponding muscle fiber;

the first raw data is configured with a linear sum of a first stimulation artifact, a first M-wave, and the vEMG signal; and the second raw data is configured with a linear sum of a second stimulation artifact, a second M-wave, and the vEMG signal.

3. The system of claim 2, wherein the processor partitions the first and second data according to a length of a frequency of the FES.

4. A method for volitional electromyography (vEMG) signal detection, the method comprising:

receiving first data from a first pair of EMG electrodes;

receiving second data from a second pair of EMG electrodes;

partitioning the first data into a plurality of first units according to a plurality of periods;

partitioning the second data into a plurality of second units according to the plurality of periods;

calculating a first data difference by subtracting an earlier first unit of the plurality of first units that corresponds to a first period of the plurality of periods from a later first unit of the plurality of first units that corresponds to a second period of the plurality of periods, the first period preceding the second period;

calculating second difference data by subtracting an earlier second unit of the plurality of second units that corresponds to the first period from a later second unit of the plurality of second units that corresponds to the second period; and detecting a vEMG signal using by subtracting the first difference data from the second difference data, wherein the detected vEMG signal is used to control a degree of stimulation of the FES.

5. The method of claim 4, wherein the first and second pairs of EMG electrodes are attached to a skin surface of a corresponding muscle, to which functional electrical stimulation (FES) is applied, in a direction parallel to a direction of a muscle fiber.

6. The method of claim 4, wherein each of the first and second data is configured with a linear sum of a stimulation artifact, an M-wave, and the vEMG signal.

7. The method of claim 4, further comprising determining the plurality of periods in consideration of a frequency of application of functional electrical stimulation (FES).

8. A system for volitional electromyography (vEMG) signal detection, the system comprising:

a functional electrical stimulation (FES) electrode configured to apply FES;

a first pair of EMG electrodes attached to a skin surface of a specific muscle to which the FES is applied;

a second pair of EMG electrodes attached to the skin surface of the specific muscle; and a circuit configured to:

partition data received from the first pair of EMG electrodes into first data for a previous FES and second data for a current FES, calculate a first data difference by subtracting the first data from the second data, partition data received from the second pair of EMG electrodes into third data for the previous FES and fourth data for the current FES, calculate a second data difference by subtracting the third data from the fourth data, and detect a vEMG signal by subtracting the first data difference from the second data difference, wherein the detected vEMG signal is used to control a degree of stimulation of the FES.

9. The system of claim 8, wherein the FES electrode, the first pair of EMG electrodes, and the second pair of EMG electrodes are each attached in a direction parallel to a direction of a muscle fiber of the specific muscle.

10. The system of claim 9, wherein:

the FES electrode includes a pair of electrodes for applying dynamic FES.

11. The system of claim 10, wherein the circuit partitions the data received from the first pair of EMG electrodes in consideration of a length of a frequency of the FES, and wherein the circuit partitions the data received from the second pair of EMG electrodes in consideration of the length of the frequency of the FES.

\* \* \* \* \*